United States Patent [19]
Johnson et al.

[11] 4,354,024
[45] Oct. 12, 1982

[54] TUNGSTEN TRIOXIDE LAYERED COMPOUNDS

[75] Inventors: Jack W. Johnson, Fanwood; Allan J. Jacobson, Princeton, both of N.J.

[73] Assignee: Exxon Research and Engineering Company, Florham Park, N.J.

[21] Appl. No.: 205,104

[22] Filed: Nov. 10, 1980

[51] Int. Cl.$^3$ .............................................. C07F 11/00
[52] U.S. Cl. ....................................... 544/181; 544/64; 544/225; 546/2; 546/10; 546/11; 546/12; 548/101; 548/109
[58] Field of Search ........................ 546/2, 10, 11, 12; 544/64, 225, 181; 548/101, 104, 109

[56] References Cited

U.S. PATENT DOCUMENTS

| | | | |
|---|---|---|---|
| 3,489,775 | 1/1970 | Seree de Roch | 260/348.5 |
| 3,688,109 | 8/1972 | Gamble | 250/51.5 |
| 3,766,064 | 10/1973 | Gamble | 252/25 |
| 4,010,217 | 3/1977 | Zuech | 260/677 |
| 4,049,887 | 9/1977 | Whittingham | 429/112 |
| 4,094,893 | 6/1978 | Pines | 260/429 R |

FOREIGN PATENT DOCUMENTS 1247594 9/1971 United Kingdom .
1377213 12/1974 United Kingdom .

OTHER PUBLICATIONS

Hersh, "Molecular Sieves", (Reingold Publishing Corp., 1961), p. 58.
McGraw Hill Dictionary of Scientific and Technical Terms, 2nd Edition, p. 899.
J. Thewlis, "Encyclopaedic Dictionary of Physics", 1961, p. 235.
Tittarelli, J. Solid State Physics 37, 95–102 (1981).
Johnson et al., J. Amer. Chem. Soc. 103, 5246–5247 (1981).
Inglis et al., Chem. Abs. 75, 20202u.
Jarels et al., Chem. Abs. 82, 155165 (1974).
Condensed Chemical Dictonary, 9th Edition, p. 436.
Hulliger, "Structural Chemistry of Layer-Type Phases", pp. 1–2.
Bernard, C. R. Acad. Sci. 263c, pp. 1068–1071, (1966).
Camelot, Nev. Chim. Min. 6, 853–883, (1969).

*Primary Examiner*—Mark L. Berch
*Attorney, Agent, or Firm*—James H. Takemoto

[57] ABSTRACT

A new composition of matter comprising layered compounds of tungsten trioxide and heterocyclic nitrogen or oxygen Lewis bases which have a unique layered structure. The layered compounds have the formula $LWO_3$ where L is a Lewis base selected from the group consisting of 5-membered heterocyclic amines, 6-membered heterocyclic amines, amine oxides, triorganophosphates, phosphine oxides and sulfoxides, the layered compounds being characterized in that L is covalently bound to a tungsten atom in the tungsten oxide layer.

9 Claims, 4 Drawing Figures

TUNGSTEN TRIOXIDE LAYERED COMPOUNDS

BACKGROUND OF THE INVENTION

This inventon relates to unique layered compounds formed by reacting tungsten trioxide hydrates or tungstic acid with a Lewis base. More particularly, amines are coordinately bound to tungsten atoms within a layered tungsten oxide structure.

It is known that tungsten halides will react with pyridine to form complex salts such as $W_2Cl_6py_4$ and $WCl_4py_2$. U.S. Pat. No. 3,489,775 describes amine tungstate salts formed by reacting tungstic acids with amines and U.S. Pat. No. 4,010,217 teaches coordination complexes of tungsten or molybdenum and nitric oxide.

It is also known that tungsten dichalcogenides can form intercalation compounds. Intercalation compounds wherein an organic isonitrile is intercalated into the layered structure of Group IVb, Vb, molybdenum and tunsten transition metal dichalcogenides where the chalcogenide is sulfur, selenium or tellurium are taught in U.S. Pat. No. 4,094,893. The general properties and methods of preparation of intercalation compounds are described in U.S. Pat. Nos. 3,766,064 and 3,688,109. As set forth therein, the intercalate occupies vacant sites within the layers of the metal chalcogenide wherein the chalcogenide is sulfur, selenium or tellurium. The intercalated species include organic and inorganic compounds which are broadly electron donors, electron acceptors, have substantial polarization interactions or are capable of d-orbital bonding. U.S. Pat. No. 4,049,887 relates to an improved cathode containing as active material, a layered compound of the formula $MA_xB_y$ where M is Fe, V, Ti, Cr, or In, A is O, S, Se or Te and B is Cl, Br or I.

Revue de Chemie Minerale, 6, 853-883 (1969) relates to an investigation of addition compounds of pyridine with the trioxides of chromium, molybdenum and uranium. These adducts have the formulas $C_5H_5N.CrO_3$, $C_5H_5N.MoO_3$ and $C_5H_5N.UO_3$. The author reports that tungsten trioxide is unreactive with pyridine at least up to 300° C.

SUMMARY OF THE INVENTION

It has been discovered that tungsten trioxide hydrate or tungstic acid can react with Lewis bases to form new compounds having a unique layered structure. The novel composition of matter comprises layered compounds of the formula $LWO_3$ where L is a Lewis base containing nitrogen or oxygen electron donors and selected from the group consisting of 5-membered heterocyclic amines, 6-membered heterocyclic amines, amine oxides, triorganophosphates, phosphine oxides and sulfoxides, the layered compounds being characterized in that L is covalently bound to a tungsten atom in the tungsten oxide layer.

In the compounds of the invention, a neutral Lewis base, such as pyridine, is strongly coordinated to a tungsten atom in the manner of a molecular coordination complex, e.g. $WCl_4py_2$. But the compounds of the invention are not molecular coordination complexes, as they possess an infinitely connected two-dimensional layered structure.

DETAILED DESCRIPTION OF THE INVENTION

Figure 1:
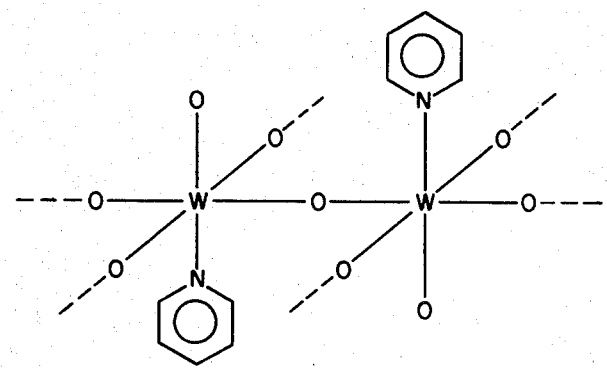
FIG. 1 is a schematic diagram of the bonding arrangement of (pyridine)$WO_3$.

The compounds of the invention comprise tungsten oxide layers which have a Lewis base inserted between the metal oxide layers and directly coordinated to tungsten. Unlike the metal chalcogenides employed in intercalation compounds, commercially obtainable $H_2WO_4$ may be used as a starting material without any pretreatment such as heat annealing or a preliminary interaction with ammonia.

Lewis bases which form the present layered compounds are those which have heterocyclic nitrogen donors and oxygen donors, preferably 5- and 6-membered heterocyclic amine donors and especially 6-membered heterocyclic amine donors. Preferred nitrogen donors are pyridines having the formula

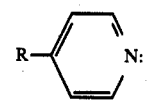

where R is hydrogen; halogen; $C_1$-$C_{20}$, preferably $C_1$-$C_{10}$ aliphatic; $C_6$-$C_{10}$ aryl, preferably phenyl which may be substituted in the 4-position by halogen or $C_1$-$C_6$ alkyl; $C_7$-$C_{20}$ aralkyl; OR' or SR' where R' is $C_1$-$C_6$ alkyl. Examples are

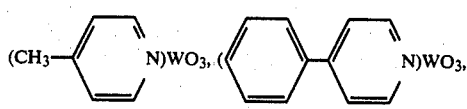

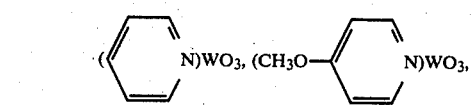

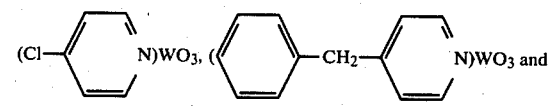

Other 5- and 6-membered heterocyclic amines which may form layered compounds include pyridazine, pyrimidine, pyrazine, triazine, N-substituted oxazine, N-substituted imidazole, oxazole and thiazole.

A Lewis base which is a bidentate heterocyclic nitrogen ligand forms compounds of the formula $L_{1/2}WO_3$, preferably compounds of the formulae

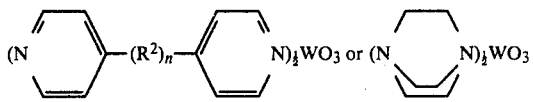

where n is 0 or 1 and $R^2$ is methylene; alkylene, alkene or alkylene of 2–6 carbon atoms; $C_6$–$C_{10}$ arylene, preferably paraphenylene; $C_7$–$C_{14}$ aralkylene, preferably

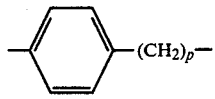

where p is from 1 to 6; oxygen; or sulfur. The bidentate ligands form connecting linkages between separate tungsten oxide layers.

Oxygen donors may be amine oxides, triorganophosphates, phosphine oxides or sulfoxides.

M. Camelot in Revue de Chemie Minerale, 6, 853–883 (1969), p. 854 reports that it is remarkable that tungsten oxide is unlike $CrO_3$, $MoO_3$ and $UO_3$ in that $WO_3$ will not react with pyridine even at very high temperatures (300° C. or more). It has been discovered that amines such as pyridine can be reacted with $H_2WO_4$ in the presence of molecular sieves. In general, $WO_3$ layered compounds may be prepared by a process which comprises placing $H_2WO_4$, Lewis base and molecular sieve in a tube, evacuating and sealing the tube, and heating at temperatures of from about 100° to 400° C. for up to 40 days. The desired product may then be isolated by cooling and opening the tube and removing the molecular sieves. The amount of amine is not critical and a stoichiometric amount or an excess may be present. Molecular sieves should be activated prior to use. Preferred reaction temperatures and times are from about 100° to 250° C. for from about 1 to 20 days. A general reaction is described as follows.

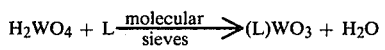

The water produced is taken up by molecular sieves.

The layered compounds of the present invention do possess the covalent bonding characteristic of molecular coordination compounds. They are not, however, molecular coordination compounds since they possess 2-dimensional extended lattices. Nor are they intercalation compounds such as are reported in U.S. Pat. No. 3,766,064. The latter compounds are generally the result of electrostatic interactions wherein the nitrogen atom of the intercalated guest is equidistant between the layers of the intercalation host and the arrangement of host atoms within the lattice is essentially unchanged.

Rather, the present layered compounds possess a unique physical structure as shown in FIG. 1 which is a schematic diagram of the bonding arrangement in

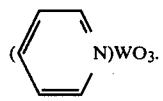

Figure 2:
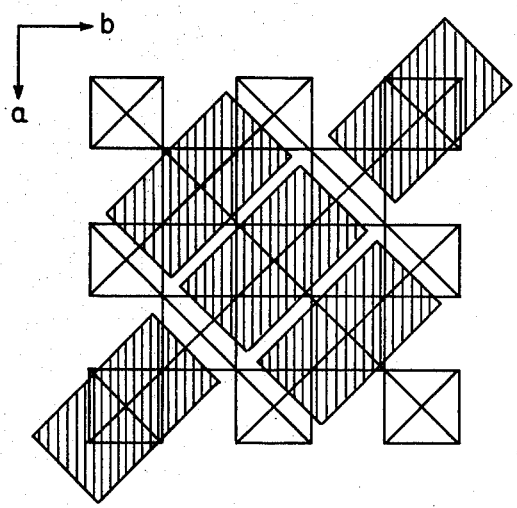
FIG. 2 is a schematic diagram of the 001 projection of (pyridine)$WO_3$ showing the van der Waals packing of the pyridine molecules.
Figure 3:
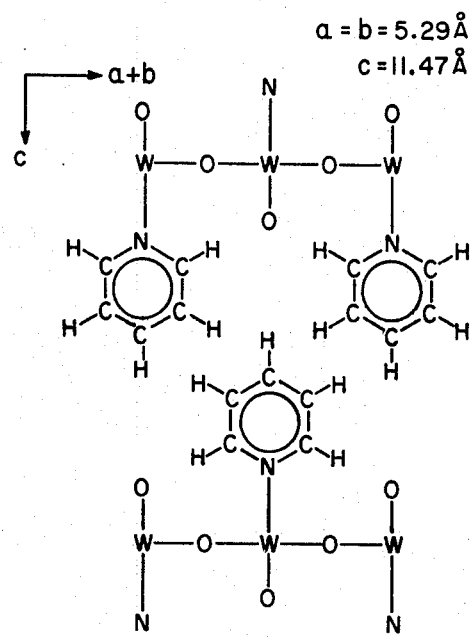
FIG. 3 is a schematic diagram of the 110 projection of the structure of (pyridine)$WO_3$.

As illustrated in this figure, pyridine occupies space between the tungsten oxide layers and bonds directly to a W atom. The overall layered structure is shown in FIGS. 2 and 3 which depict the 001 projection of the structure of

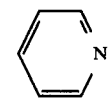

showing van der Waals packing of the

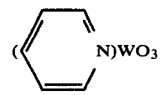

molecules as designated by the cross-hatching and the 110 projection of

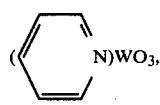

respectively. The nature of L determines the separation of $WO_3$ layers, e.g., (pyridine)$WO_3$ has an interlayer separation of 11.5 Å, and (4-phenylpyridine)$WO_3$ a separation of about 20.7 Å. As can be seen from the figures, the layers are composed of $WO_5L$ octahedra sharing corner oxygen atoms. The Lewis base is trans to the single unshared oxygen. Based on x-ray studies, it can be determined that in order for the Lewis base to bond to W atoms, it must meet the steric requirement such that the cross-sectional area of the Lewis base perpendicular to an axis running through the Lewis base-W covalent bond is less than about 30 (Å)$^2$. Thus bulky Lewis bases such as triethylamine or triphenylphosphine will not form layered compounds according to the invention, because of the above-mentioned structural considerations.

Figure 4:
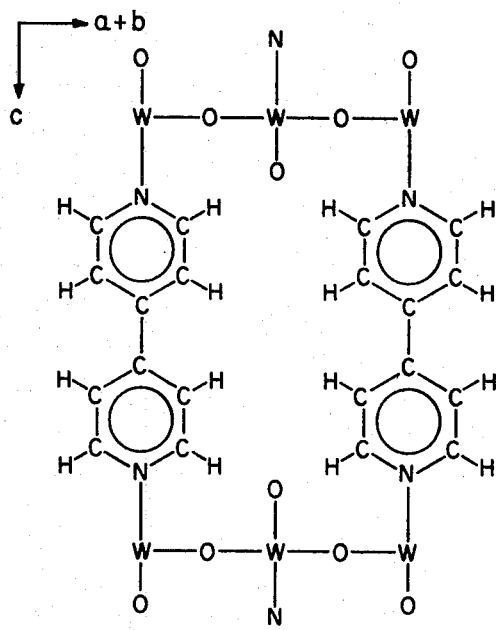
FIG. 4 is a schematic diagram of the bonding arrangement of (4,4'-bipyridine)$WO_3$.

When a bidentate Lewis base is incorporated into the $LWO_3$ structure, separate tungsten oxide layers can be bound together. For example, when 4,4′-bipyridine is employed, each separate pyridine ring can bind to tungsten atoms in adjacent tungsten oxide layers, thus forming a composition wherein individual layers within the overall $LWO_3$ crystal structures are bound together by bridging 4,4′-bipyridine molecules. This is shown schematically in FIG. 4. These bridged layered compounds are unique in that they exhibit a higher degree of thermal stability than the corresponding unbridged compounds.

The pure $LWO_3$ product shows no lines characteristic of the starting materials in an x-ray powder pattern analysis. The x-ray analysis further demonstrates that the interlayer distance correlates with the size of specific Lewis bases between the layers. Thermogravimetric analysis indicates the loss of Lewis base corresponding to a 1:1 or 2:1 $MoO_3$:L composition. The 2:1 ratio reflects a bridging ligand such as 4,4′-bipyridine.

Layered compounds according to the invention possess unique properties. First, they have a 2-dimensionally bonded layered structure with tungsten in its highest oxidation state. Their color is pale in contrast to the dark opaque colors of intercalation compounds of $WO_3$, which compounds have 3-dimensional structures. The present layered compounds are useful in electrochromic devices and as lithium battery cathodes.

The following examples are further illustrative of the invention.

EXAMPLE 1

The preparation of WO$_3$(pyridine) is described as follows. H$_2$WO$_4$ was heated in a sealed tube with an excess of dry pyridine in the presence of activated 4 A molecular sieves at 150° C. for 7-14 days. The resulting pale green solid was shown by thermogravimetric (TGA) and chemical analysis to contain approximately one equivalent of pyridine per WO$_3$. The x-ray powder diffraction pattern could be fully indexed in the tetragonal system with lattice parameters a =5.29 Å and c=11.47 Å. The infrared spectrum contained bands at 1647, 1605, 1572, 1488, 1446, 1239, 1220, 1154, 1141, 1063, and 1042 cm$^{-1}$ which are typical of coordinated pyridine. The pyridine is quantitatively lost upon heating to 275° C. The high temperature required to release the pyridine (boiling point 115° C.) indicates that it is strongly bound into the lattice, rather than physically adsorbed.

EXAMPLE 2

A layered compound containing DABCO (1,4-diazabicyclo[2.2.2]octane=

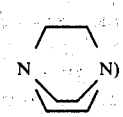

is prepared by heating H$_2$WO$_4$ in a sealed tube with an excess of sublimed DABCO in dry toluene in the presence of activated 4 A molecular sieves at 150° C. for 18 hr. The resulting blue-green solid product was shown by TGA to contain 0.50 equivalent of DABCO per mole of WO$_3$. The DABCO is lost in a sharp exothermic reaction upon heating to 235° C. in oxygen. Since DABCO itself sublimes below 100° C., the weight loss at 235° C. indicates its incorporation into the lattice. X-ray powder diffraction showed broad low angle lines at d spacings of 11.0 and 9.4 Å.

EXAMPLE 3

The incorporation of 4,4'-bipyridine into the layered structure of WO$_3$ is accomplished by heating H$_2$WO$_4$ in a sealed tube with excess sublimed 4,4'-bipyridine in dry toluene in the presence of activated 4 A molecular sieves at 150° C. for 15 days. The green solid product had incorporated 0.20 equivalent of 4,4'-bipyridine that was lost in the temperature range 200°-500° C. in the TGA analysis. A powder x-ray diffraction diagram showed strong lines at 11.6, 3.73, and 2.64 Å d spacings and less intense lines at 5.69, 3.36, and 3.12 Å.

EXAMPLE 4

This example is directed to a layered compound containing a 4-substituted pyridine, i.e. 4-phenylpyridine. H$_2$WO$_4$ was heated in a sealed tube with excess dry 4-phenylpyridine, toluene and activated 4 A molecular sieves at 180° C. for about 4 days. Thermogravimetric analysis of the blue-colored product showed a weight loss in the temperature range 250°-450° C. corresponding to 0.5 mole 4-phenylpyridine per mole WO$_3$. Powder x-ray diffraction indicated a layer separation of 20.7 Å.

EXAMPLE 5

An example of the incorporation of a 5-membered heterocyclic amine into the WO$_3$ layered structure is WO$_3$(N-methylimidazole). The preparation of this layered compound was achieved by heating H$_2$WO$_4$ in a sealed tube with excess N-methylimidazole and activated molecular sieves for 4 days at 160° C. The resulting green solid product showed a weight loss in the temperature range 100°-450° C. corresponding to 0.87 mole N-methylimidazole per mole WO$_3$. Powder x-ray diffraction showed a broad low angle peak at 10.5-11.0 Å. The same reaction run at 125° C. for 22 days gave a similar product that contained 0.76 equivalent N-methylimidazole per WO$_3$.

What we claim is:

1. A composition of matter comprising layered compounds containing WO$_3$ and nitrogen donor Lewis bases, said layered compounds having the formula

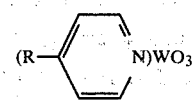

wherein R is hydrogen; halogen; C$_1$-C$_{20}$ aliphatic hydrocarbon; C$_6$-C$_{10}$ aryl; C$_7$-C$_{20}$ aralkyl; OR' or SR' where R' is C$_1$-C$_6$ alkyl, the layered compounds being characterized in that

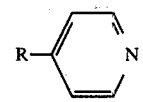

is covalently bound to a tungsten atom in the tungsten oxide layer.

2. A composition of matter comprising layered compounds containing WO$_3$ and nitrogen donor Lewis bases, said compounds having the formula LWO$_3$ where L is a Lewis base selected from the group consisting of pyridine, pyridazine, pyrimidine, pyrazine, triazine, and N-methyl imidazole, the layered compounds being characterized in that L is covalently bound to a tungsten atom in the tungsten oxide layer.

3. A composition of matter comprising bridged layered compounds containing WO$_3$ and nitrogen donor Lewis bases, said layered compounds having the formula

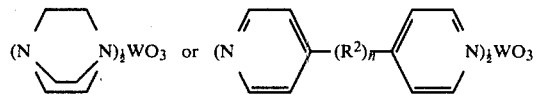

where n is 0 or 1 and R$^2$ is methylene or alkylene, alkenylene or alkynylene of 2-6 carbon atoms; C$_6$-C$_{10}$ arylene; C$_7$-C$_{14}$ aralkylene; oxygen or sulfur, the bridged layered compounds being characterized in that the nitrogen donor Lewis base is covalently bound to tungsten atoms in separate tungsten oxide layers.

4. The composition of claim 3 wherein R$^2$ is methylene; alkylene of 2-6 carbon atoms; paraphenylene;

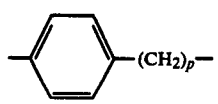

where p is from 1 to 6; oxygen or sulfur.

5. The composition of claim 3 wherein the layered compound is

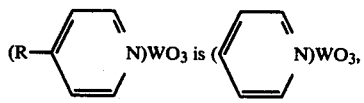

6. The composition of claims 1, 2 or 3 wherein the Lewis base has the steric requirement such that the maximum cross-sectional area of the Lewis base perpendicular to an axis running through the Lewis base-W covalent bond is less than about 30 (Å)$^2$.

7. The composition of claim 1 wherein

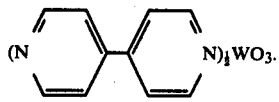

-continued

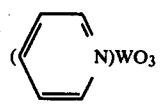

8. A compositon of matter comprising layered compounds of the formula characterized in that pyridine is covalently bound to a tungsten atom in the tungsten oxide layer.

9. A method for preparing the layered compounds of claims 1, 2 or 3 which comprises contacting H$_2$WO$_4$ and Lewis base with activated molecular sieves in a sealed tube and heating at temperatures of from about 100° C. to 400° C. for up to 40 days.

* * * * *